United States Patent
Petrov et al.

(10) Patent No.: US 6,653,419 B1
(45) Date of Patent: Nov. 25, 2003

(54) POLYFLUORINATED EPOXIDES AND ASSOCIATED POLYMERS AND PROCESSES

(75) Inventors: Viacheslav Alexandrovich Petrov, Hockessin, DE (US); Andrew Edward Fiering, Wilmington, DE (US); Jerald Feldman, Hockessin, DE (US)

(73) Assignee: E. .I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/009,037

(22) PCT Filed: May 1, 2000

(86) PCT No.: PCT/US00/11746

§ 371 (c)(1),
(2), (4) Date: Oct. 3, 2001

(87) PCT Pub. No.: WO00/66575

PCT Pub. Date: Nov. 9, 2000

Related U.S. Application Data

(60) Provisional application No. 60/132,453, filed on May 4, 1999.

(51) Int. Cl.[7] .......................... C08F 16/12; C08F 216/20
(52) U.S. Cl. ...................... 526/247; 526/242; 526/243; 528/408; 528/417; 528/421; 549/519; 549/523; 549/524; 549/539; 549/563
(58) Field of Search .............................. 549/519, 523, 549/524, 539, 563; 526/242, 243, 247; 528/408, 417, 421

(56) References Cited

U.S. PATENT DOCUMENTS

| 3,275,573 A | 9/1966 | Vandenberg |
| 3,573,330 A | 3/1971 | Dear et al. |
| 4,965,379 A | * 10/1990 | Ikeda |
| 5,084,583 A | 1/1992 | Rozen et al. |
| 5,808,132 A | 9/1998 | Sonoi et al. |

FOREIGN PATENT DOCUMENTS

| EP | 0064293 A1 | 11/1982 |
| EP | 0100488 A1 | 2/1984 |
| EP | 0414569 A2 | 2/1991 |
| EP | 0473398 A1 | 3/1992 |
| EP | 0889028 A2 | 1/1999 |
| JP | 96333302 | 12/1996 |
| WO | WO 0017712 | 3/2000 |
| WO | WO 0067072 | 11/2000 |

OTHER PUBLICATIONS

Richard D. Chambers et al., Syntheses of Perfluorinated Epoxides, Diepoxides, and a Novel Rearrangement, *Research on Chemical Intermediates*, 1996, vol. 22, No. 8, pp. 703–715.

L.V. Saloutina et al., Synthesis of Polyfluoroalkylated 1,4–diazinols and 1,4–oxazinols using polyfluoro–2,3–epoxyalkanes 32 + 13, *Journal of Fluorine Chemistry*, vol. 87, No. 1, pp. 49–55.

XP002145136 Simmons H. E.: "Fluoroketones" Journal of the American Chemical Society, vol. 82, No. 9, 1960, pp. 2288–2296, American Chemical Society, Washington, DC, US ISSN: 0002-7863 p. 2294, right hand col., last paragraph.

XP002145137 Bryce M.R.: "Reacation involving fluoride ion. Part 30. Preparation and reactions of epoxides derived from perfluoroalkyl substituted alkenes" Journal of the Chemical Society, Perkin Transactions 1., No. 7, 1984, pp. 1391–1395, Chemical Society. Letchworth., GB ISSN: 1470–4358 compound of formula 6 in pp. 1391–1392 and 1394.

XP002145138 Golubev A.S.: "Cycloaddition reactions of the methyl ester of trifluoropyruvic acid" Bulletin of the Academy of Sciences of the USSR. Division of Chemical Science., vol. 37, No. 1, Jul. 20, 1988 pp. 117–121, Concultants Bureau, New York., US compound of formula II in pp. 117 and 119.

XP002154159 Database WPI Section Ch, Week 199425 Derwent Publications Ltd., London, GB; Class A25, AN 1994–206550 & JP 06145338 A (Japan) Energy KK), May 24, 1994 abstract.

Chang, I.S., Willis, C. J., Can. J. Chem. 1997, 55, 2465.

Kolenko, I. P., Filaykova, T. I., Zapevalov, A. Yu., Lur'e, E.P. Izv. AN USSR. Ser. Khim. 1979, p. 2509.

Coe, P. L. Mott, A. W., Tatlow, J.C., J. Fluorine Chemistry, 1985, V30, p. 297.

* cited by examiner

Primary Examiner—Robert Dawson
Assistant Examiner—D. Aylward

(57) ABSTRACT

A method for producing partially fluorinated epoxides and corresponding polyether homopolymers of these polyfluorinated epoxides is described. Also described is a method for incorporating a fluoroalcohol functional group into a polymer as a pendant group. Certain perfluorinated olefins are also described. These polyfluorinated epoxides and the associated polymers and methods relating to them are useful components in photoresists, particulary in lithographic photoresists for use at low ultraviolet wavelengths (e.g., 157 nm).

12 Claims, No Drawings

POLYFLUORINATED EPOXIDES AND ASSOCIATED POLYMERS AND PROCESSES

This application claims the benefit of Provisional application No. 60/132,453 filed May 4, 1999.

BACKGROUND OF THE INVENTION

1. Field of the Invention

This invention is in the field of polyfluorinated epoxides and includes methods for producing these epoxides, certain chemical reactions these epoxides undergo, and monomers and polymers derived from these epoxides and/or their derivatives.

2. Description of Related Art

Various polyfluorinated epoxides are known. As an illustrative example, 1,1-bis(trifluoromethyl)ethylene oxide is known and can be produced by reaction of diazomethane and hexafluoroacetone: see Chang, I. S., Willis, C. J., Can. J. Chem. 1997, 55, 2465. While this production method can be done on a lab scale, it does involve use of hazardous diazomethane and is not capable of being scaled up for producing larger quantities. As a second illustrative example, the compound illustrated below is also known.

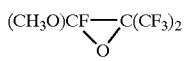

The production of this compound, again involving a hazardous reagent, has been reported via oxidation of the corresponding olefin with ozone. See JP Patent Publication 08333302 A2. Neither of the aforementioned production processes is attractive for commercial production for the reasons presented above.

The preparation of perfluorinated or perhalogenated epoxides using sodium hypochlorite or sodium hypobromide is known. See: Kolenko, I. P., Filaykova, T. I., Zapevalov, A. Yu., Lur'e, E. P. Izv. AN USSR. Ser. Khim. 1979, p. 2509; and Coe, P. L., Mott, A. W., Tatlow, J. C., J. Fluorine Chemistry, 1985, V30, p. 297.

There is a need for a safe and efficient production method for producing polyfluorinated epoxide compounds as well as safe efficient processes for converting them into useful polymeric products.

SUMMARY OF THE INVENTION

In one embodiment, the invention is a method for producing a fluorinated epoxide in high yield, said method comprising the step of reacting a fluorinated ethylenically unsaturated compound having the structure:

$$(R_1)(R_2)C=C(R_3)(R_4)$$

with a metal hypohalite oxidizing agent in the presence of a phase transfer catalyst to produce the fluorinated epoxide having the structure:

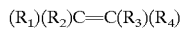

wherein $R_1$ is selected from the group consisting of H and OR, where R is $C_1$–$C_{10}$ alkyl; $R_2$ is selected from the group consisting of H and F; and $R_3$ and $R_4$ are selected from the group consisting of $C_1$–$C_{10}$ perfluoroalkyl and $C_1$–$C_{10}$ perfluoroalkoxy.

In another embodiment, the invention is a method for producing a fluorinated epoxide in high yield, said method comprising the step of reacting a fluorinated ethylenically unsaturated compound having the structure:

with a metal hypohalite oxidizing agent in the presence of a phase transfer catalyst to produce the fluorinated epoxide having the structure:

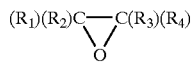

wherein $R_1$ is selected from the group consisting of H and OR, where R is $C_1$–$C_{10}$ alkyl; $R_2$ is selected from the group consisting of H, F, $C_1$–$C_{10}$ perfluoroalkyl, and X-substituted $C_1$–$C_{10}$ alkyl, wherein X is F, Cl, Br, I, OH, or OR; $R_3$ and $R_4$ are each independently selected from the group consisting of $C_1$–$C_{10}$ perfluoroalkyl.

In another embodiment, the invention is a method for producing a fluorinated epoxide in high yield, said method comprising the step of reacting a fluorinated ethylenically unsaturated compound having the structure:

$$(R_1)(R_2)C=C(R_3)(R_4)$$

with a metal hypohalite oxidizing agent in the presence of a phase transfer catalyst to produce the fluorinated epoxide having the structure:

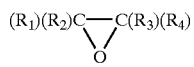

wherein $R_1$ is selected from the group consisting of H and OR, where R is $C_1$–$C_{10}$ alkyl; $R_2$ is selected from the group consisting of H, F, $C_1$–$C_{10}$ perfluoroalkyl, and X-substituted $C_1$–$C_{10}$ alkyl, wherein X is F, Cl, Br, I, OH, or OR; $R_3$ and $R_4$ are each independently selected from the group consisting of $C_1$–$C_{10}$ perfluoroalkyl, $C(R_f)(R_f')OH$ where $R_f$ and $R_f'$ are $C_1$–$C_{10}$ perfluoroalkyl groups, $C_1$–$C_{10}$ perfluoroalkoxy, $C_1$–$C_{10}$ carboalkoxy, and hydroxy-substituted $C_3$–$C_{10}$ carboalkoxymethyl-substituted $C_1$–$C_4$ perfluoroalkyl.

In another embodiment, the invention is a fluorine-containing polymer comprising a repeat unit derived from at least one ethylenically unsaturated compound containing a fluoroalcohol functional group having the structure:

$$\text{—XCH}_2\text{C}(R_f)(R_f')\text{OH}$$

wherein $R_f$ and $R_f'$ are the same or different fluoroalkyl groups of from 1 to about 10 carbon atoms or taken together are $(CF_2)_n$ wherein n is 2 to 10; and X is selected from the group consisting of sulfur, oxygen, nitrogen, phosphorous and any other element selected from Group Va and Group VIa.

In yet another embodiment, the invention is a perfluorinated epoxide having the structure:

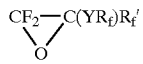

where $R_f$ and $R_f'$ are the same or different perfluoroalkyl groups of from 1 to about 10 carbon atoms or taken together are $(CF_2)_n$ wherein n is 2 to 10; and Y is selected from the group consisting of sulfur and oxygen.

In still another embodiment, the invention is a method for incorporating a fluoroalcohol functional group having the structure:

—XCH$_2$C(R$_f$)(R$_f'$)OH into a polymer as a pendant group, wherein R$_f$ and R$_f'$ are the same or different fluoroalkyl groups of from 1 to about 10 carbon atoms or taken together are (CF$_2$)$_n$ wherein n is 2 to 10; and X is selected from the group consisting of sulfur, oxygen, nitrogen, phosphorous and any other element selected from Group Va and Group VIa;
said method comprising the steps of:
  a. reacting an epoxide having the structure:

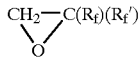

with an ethylenically unsaturated compound containing substituent X to produce an ethylenically unsaturated comonomer comprised of the structure:

—XCH$_2$C(R$_f$)(R$_f'$)OH;

and
  b. polymerizing a reaction mixture comprised of the ethylenically unsaturated comonomer to produce the polymer.

In still another embodiment, the invention is a compound of structure

R$_a$XCH$_2$C(R$_f$)(R$_f'$)OH where R$_a$ is an ethylenically unsaturated alkyl group of from 2 to 20 carbon atoms, optionally substituted by one or more ether oxygens and R$_f$ and R$_f'$ are the same or different perfluoroalkyl groups of from 1 to about 10 carbon atoms or taken together are (CF$_2$)$_n$ wherein n is 2 to 10, and X is selected from the group consisting of sulfur, oxygen, nitrogen, phosphorous and any other element selected from Group Va and Group VIa.

DETAILED DESCRIPTION OF THE PREFERRED EMBODIMENT(S)

In one embodiment, the invention is a method for producing a fluorinated epoxide comprising the step of reacting a fluorinated ethylenically unsaturated compound (structure given supra) with a metal hypohalite oxidizing agent in the presence of a phase transfer catalyst to produce the fluorinated epoxide (structure also given supra).

A suitable oxidizing agent is a metal hypohalite. Exemplary metal hypohalites include, but are not limited to, various metal hypochlorites or metal hypobromites, including lithium, sodium, potassium, and calcium hypochlorites or hypobromites. Preferred oxidizing agents are sodium, calcium, or potassium hypochlorite and sodium or potassium hypobromite.

Examples of suitable phase-transfer catalysts include, but are not limited to, tetraethylammonium chloride, tetraethylammonium bromide, tetramethylammonium hydroxide, tetrabutylammonium chloride, tetrabutylammonium bromide, tetrabutylammonium hydroxide, trimethylbenzylammonium chloride, trimethylbenzylammonium bromide, methyltricaprylyl halide, methyltricaprylyl hydroxide, and trimethylbenzylammonium hydroxide. Preferred are methyltricaprylyl halide or hydroxide.

In another embodiment, the invention is a method for producing a polyfluorinated polyether comprising the step of reacting a fluorinated epoxide having the structure given supra with a basic compound in solvent or neat to produce the polyfluorinated polyether as given supra. Suitable bases for use in this reaction include, but are not limited to, trialkylamines of formula R$_1$R$_2$R$_3$N, where R$_1$–R$_3$ are independently C$_1$–C$_6$ alkyl; pyridine, sodium or potassium alkoxides (e.g., methoxide, ethoxide, t-butoxide), and sodium or potassium hydroxide.

The polyfluorinated epoxides of this invention having the structure:

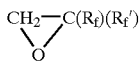

can be reacted with a variety of compounds (as illustrated in Examples 3–6, 8) to afford new compounds comprised of the structure:

—X—CH$_2$C(R$_f$)R$_f'$)OH

GLOSSARY

Term "F—" in a compound name designates that the compound is perfluorinated.

EXAMPLES

Example 1

Preparation of 1,1-Bis(trifluoromethyl)ethylene Oxide (1)

Hexafluoroisobutene CH$_2$=C(CF$_3$)$_2$ (25 ml, 40 g) was condensed in a flask containing a solution of NaOCl (made at −5 to −3° C. by bubbling 15 g of chlorine into mixture of 50 ml of 50 wt. % of NaOH and 100 ml of water) and 0.5 g of phase transfer catalyst—methyltricaprylylammonium chloride (Aliquat™-336, Aldrich) was added at −2 to +2° C. under vigorous stirring. Reaction mixture was agitated at this temperature for 1–1.5 hours.

The resulting reaction product was transferred out of the reactor in vacuum, collected in a cold trap (at −78° C.) and distilled to give 37.5 g (yield 86%) of liquid, b.p. 41–42° C./760 mm Hg, which was identified as 1,1-bis (trifluoromethyl)ethylene oxide (1). The resulting compound 1 was established to have the indicated structure based upon the analytical data obtained as indicated below.

$^1$H NMR: 3.28 (s) ppm; $^{19}$F NMR: −73.34 (s) ppm; $^{13}$C {H} NMR: 46.75 (s), 54.99(sept, 37 Hz), 126.76 (q, 275 Hz) IR (gas, major): 1404 (s), 1388 (s), 1220 (s), 1083 (s), 997 (m), 871 (m), 758 (w), 690 (m), 636 (w) cm$^{-1}$; Anal. Calcd for C$_4$H$_2$F$_6$O: C, 26.68, H, 1.12. Found: C, 27.64, H, 1.10.

Example 2

Synthesis of CH$_2$=CHOCH$_2$CH$_2$OCH$_2$C(CF$_3$)$_2$OH (2)

A dry 5-L round bottom flask equipped with mechanical stirrer, condenser and addition funnel was flushed with nitrogen and charged with 14.2 g (0.59 mol) of 95% sodium hydride and 400 mL of anhydrous DMF. This mixture was cooled to 10° C. and 41.6 g (1.85 g, 0.47 mol) of 2-hydroxyethylvinyl ether was added dropwise over ½ hr. An additional 250 mL of DMF were added and the mixture was stirred for 1 hr. 1,1-Bis(trifluoromethyl)ethylene oxide (1, Hexafluoro-isobutylene epoxide) (85 g, 0.47 mol) was added over 1 hr at 20–23° C. The resulting suspension was stirrer for 22 hr. It was then transferred to a one-neck flask and most of the DMF was removed on a rotary evaporator at 0.1 mm and 29° C. The residue was dissolved in 250 mL of water and 10% hydrochloric acid was carefully added until the solution pH was about 8. An oil which separated was collected, washed with water and dried over a mixture of anhydrous sodium sulfate and potassium carbonate. The mixture was filtered and the filtrate was distilled in a Kugelrohr apparatus at 0.5 mm and 50–59° C. from a small amount of anhydrous potassium carbonate to give 89 g (71%) of oil which was stored over potassium carbonate and characterized to be compound 2. $^1$H NMR ($\delta$, $C_6D_6$) 3.12 (d, 2H), 3.28 (d, 2H), 3.60 (s, 2H), 3.90 (d, 1H), 4.07 (d, 1H), 6.20 (dd, 1H). $^{19}$F NMR ($\delta$, $C_6D_6$) −76.89 (s).

Example 3

Reaction of 1 with $(CH_3)_3COK$ 18 g of 1 was added dropwise to a solution of 12 g $(CH_3)_3COK$ in 100 ml of dry dimethylformamide over period of 1 h to keep temperature of reaction mixture at 5 to 10° C. After addition was finished the reaction mixture was allowed to warm up to 25° C. and kept at this temperature for 1 h. The reaction mixture was poured into a 200 ml of cold solution of 10% hydrochloric acid, extracted with $CH_2Cl_2$ (2×50 ml), dried over $MgSO_4$, solvent was removed and the residue was distilled to give 13.5 g of liquid b.p. 139–140° C., which is the product $(CH_3)_3COCH_2C(CF_3)_2$OH, 95% purity.

$^1$H NMR: 1.26 (3H, s), 3.80 (2H, s), 4.20 (1H, br s) ppm; $^{19}$F NMR: −76.24 (s) ppm.

Example 4

Reaction of 1 with $C_6H_5NH_2$ 15 g of 1 was added dropwise to 10 ml of $C_6H_5NH_2$ with stirring over period of 1 h to keep temperature of reaction mixture below 25° C. After addition was finished the reaction mixture was allowed to warm up to 25° C., kept at this temperature for 16 h and distilled to give 15 g of material b.p. 112–113° C./10 mm Hg, which crystallized upon standing, m.p. 34–35° C. The product has a structure $C_6H_5NHCH_2C(CF_3)_2OH$.

$^1$H NMR: 3.75 (2H, s), 4.30 (1H, br s), 4.20 (1H, br s), 6.80 (2H, d), 6.95 (1H, t), 7.32 (2H, t) ppm; $^{19}$F NMR: −77.92 (s) ppm; Anal. Calcd for $C_{10}H_9F_6NO$: C, 43.97, H, 3.32, F, 41.73, N, 5.13. Found: C, 43.46, H, 3.26, F, 40.53, N, 5.09.

Example 5

Reaction of 1 with 4-F—$C_6H_4NH_2$ 10 g of 1 was added dropwise to a solution of 5 g of 4-F—$C_6H_4NH_2$ in 10 ml of $CH_2Cl_2$ with stirring. After addition finished the reaction mixture was allowed to warm up to 25° C., kept at this temperature for 16 h, solvent was removed, the residue was distilled to give 12 g of material b.p. 116.5–118.5° C./12 mm Hg, which crystallized upon standing, m.p. 34–36° C. The product has a structure 4-F—$C_6H_4NHCH_2C(CF_3)_2OH$.

$^1$H NMR: 3.64 (2H, s), 4.20 (2H, br s), 6.80 (2H, d), 6.75 (2H, m), 6.93 (2H, t) ppm; $^{19}$F NMR: −77.94 (6F, s), −123.08 (1F, m) ppm; Anal. Calcd for $C_{10}H_8F_7NO$: C, 41.25, H, 2.77, F, 45.67, N, 4.81. Found: C, 41.00, H, 2.70, F, 45.78, N, 4.73.

Example 6

Reaction of 1 with $C_6F_{13}CH_2CH_2SH$ 4.5 g of 1 was added dropwise with stirring to a solution of 9.5 g of $C_6F_{13}CH_2CH_2SH$ in 50 ml of dry dimethylformamide, to keep temperature below 25° C. After addition finished the reaction mixture was kept at 25° C. for 16 h, poured into 100 ml of cold solution of 10% solution of HCl, the organic layer was separated, dried over $P_2O_5$ and distilled to give 6 g of material b.p. 25–26° C./0.1 mm Hg. The product has a structure $C_6F_{13}CH_2CH_2SCH_2C(CF_3)_2$OH.

1H NMR: 2.50 (2H, m), 2.88 (2H, m), 3.18 (2H, s), 4.15 (1H, br s), ppm; $^{19}$F NMR: −77.90 (6F, s), −81.39 (3F, tt), −114.60 (2F, m), −122.36 (2F, m, −123.34 (2F, m), −123.83 (2F, m), −126.64 (2F, m) ppm.

Example 7

Reaction of 1 with $C_6H_6$ 10 g of 1 was added dropwise at I10° C. to a mixture of 20 g Of $C_6H_6$ and 0.5 g of anhydrous $AlCl_3$, stiffed at 10° C. for 1 h and poured on ice. Organic layer was separated, dried over $MgSO_4$ and distilled to give 9 g of material b.p. 101–103/53 mm Hg, which was found to be $C_6H_5CH_2C(CF_3)_2OH$.

$^1$H NMR: 2.75 (1H,br s), 3.31 (211, s), 7.28 (2H, m), 7.42 (3H, m)ppm; $^{19}$F NMR: −75.39 (s) ppm; Anal. Calcd forg $C_{10}H_8F_6O$: C, 45.53,11, 3.12, F, 44.15. Found: C, 46.30, H, 3.32, F, 43.94.

Example 8

Reaction of 1 with $HOSO_2CF_3$ 4 g of 1 was added dropwise at 10° C. to 10 ml of $HOSO_2CF_3$ to keep temperature below 30° C. The reaction mixture was stirred at 25° C. for 3 h and poured on ice. Organic layer was separated, dried over $MgSO_4$ and distilled to give 8 g of material, which was found to be $CF_3SO_2OCH_2C(CF_3)_2OH$.

$^1$H NMR: 4.53 (2H,br s), 3.31 (111, br s) ppm. $^{19}$F NMR: −74.74 (3F, s), −76.24 (6F, s) ppm; IR (major): 3507 (m), 1426 (s), 1226 (s), 1146 (s), 982 (s), 823 (w) cm$^{-1}$.

Example 9

Prelaration of 1-Methoxy-F-2,2-dimethylethylene Oxide

Olefin $CH_3OCF=C(CF_3)_2$(4.8 g) was added dropwise into a flask containing a solution of NaOCl (made at −5 to −3° C. by addition of 2.5 ml of chlorine into solution of 10 ml 50% NaOH in 20 ml of water) and 0.3 g of phase tranfer catalyst—methyl tricaprylyl ammoniumn chloride (Aliquat™-336, Aldrich) at −2 to 0° C. under vigorous stirring. Reaction mixture was kept at this temperature for 40 min, diluted with water, organic layer (lower) was separated, washed with water, dried over $MgSO_4$ and analyzed. Based on NMR data crude product was found to be a mixture of 80% of 1-methoxy-F-2,2-dimethylethylene oxide and 20% of $(CF_3)_2CClC(O)OCH_3$.

Epoxide: $^1$H NMR: 3.53 (d, 1 Hz) ppm. $^{19}$F NMR: −69.06 (3F, dt, 8; 19 HZ), −64.40 (3F, qd, 8; 1 Hz), −110.90 (1F, m)ppm. IR: 1490 (s, epoxide), cm$^{-1}$.

Comparative Example 1

Attempt of Oxidation of $C_4F_9CH=CH_2$

In an attempted reaction of 5 g of $C_4F_9CH=CH_2$ with solution of NaOCl (prepared from 10 ml of 50% NaOH, 20 ml of $H_2O$ and 3 ml of chlorine) and 0.3 g of phase transfer catalyst—methyltricaprylylammonium chloride (Aliquat™-336, Aldrich) at −2 to 0C for 2 h only starting fluoroolefin was recovered and no detectable reaction products were found.

Example 10

Preparation of F-1-Methyl-1-n-Prolpylethylene Oxide

Olefin $CF_2=C(OC_3F_7\text{-n})CF_3$ (60 g) was added dropwise into a flask containing a solution of NaOBr (made at −5 to −3° C. by addition of 12 ml of bromine into solution of 20 g NaOH in 150 ml of water) and 100 ml of $CH_3CN$ at −2 to 0° C. under vigorous stirring. Reaction mixture was kept at this temperature for 4 hours, diluted with water, organic layer (lower) was separated, washed with water, dried over $P_2O_5$ and distilled to give 54 g (yield 86%) of liquid, b.p. 56–57° C., identified as F-1-methyl-1-n-propoxyethylene oxide.

$^{19}F$ NMR: −79.57 (3F, s), −85.81 (3F, t), −87.29 (2Fm), −114.59 (2F, m), −134.00 (2F, m) ppm. IR: 1517 (s), epoxide, $cm^{-1}$.

Example 11

Polymerization of 1,1-Bis(trifluoromethyl)ethylene Oxide

To 5 g of epoxide (1) in a glass reactor 2 drops of dry triethylamine were added and glass reactor was left at 25° C. After 12 hours no liquid, but only white solid was found inside of reactor. The material was not soluble in solvents such as tetrahydrofuran or diglyme, CFC-113, but it was slightly soluble in acetone and fairly soluble in $C_6F_6$. Data of $^1H$, $^{19}F$ and $^{13}C$ NMR of polymer solution in $C_6F_6$ are consistent with the structure of polyether (i.e., ring opened polymer having the structure shown below:

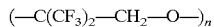

Molecular weight calculated based on NMR data was in the range 3000–5000. Based on DSC, this polymer has a sharp melting point at 148.8° C. (second heat) and started to decompose at temperature over 350° C.

Example 12

Synthesis of

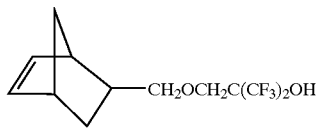

Hexafluoroisopropanol-substituted Norbornene

A dry round bottom flask with mechanical stirrer and condenser was charged under nitrogen with 28.8 g (1.2 mol) of 95% sodium hydride and 400 ml of anhydrous DMF. 5-Norbornene-2-methanol (108.6 g, 0.875 mol) was added dropwise at room temperature over 0.5 hr. The resulting mixture was stirred for 3 hr. 1,1-Bis(trifluoromethyl) ethylene oxide (1,Hexafluoroisobutylene epoxide) (173.2 g, 0.96 mol) was added dropwise over 2 hr. The resulting mixture was stirred for 72 hr at room temperature. DMF was evaporated on a rotary evaporator at 45° C. and 1 mm. The residue was diluted with 300 mL of ice water containing 30 mL of glacial acetic acid. A lower layer was separated and the aqueous layer was extracted with 2×25 ml of methylene chloride. The combined organic layers were washed with 3×100 ml of water, dried over anhydrous magnesium chloride, filtered and distilled under vacuum in a Kugelrohr apparatus at 65–87° C. and 0.1 mm. An NMR spectrum revealed that the product was contaminated with small amounts of DMF so it was dissolved in 100 ml of hexane, washed with 4×200 ml water, dried over anhydrous magnesium sulfate, filtered and distilled in a Kugelrohr apparatus at 70–80° C. and 0.1 mm giving 233.9 g (88%) of the title product (hexafluoroisopropanol-substituted norbornene, compound 3). In another preparation, the product was distilled through a 12" Vigreux column indicating a bp of 52–53° C. at 0.1 mm. $^1H$ NMR ($\delta$, $CD_2Cl_2$) 0.5 to 4.3 (complex multiplets, 12H), 5.90, 6.19 and 6.26 (m, 2H). $^{19}F$ NMR ($\delta$, $CD_2Cl_2$) −77.4 (s).

Example 13

Copolymedzation of

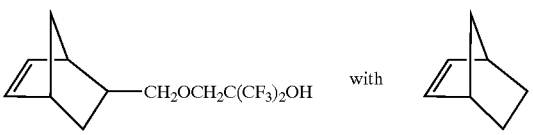

by Vinyl-addition Polymerization

Under nitrogen, 0.125 g (0.319 mmol) of allyl palladium complex $[(\eta^3\text{-MeCHCHCH}_2)PdCl]_2$ and 0.219 g (0.637 mmol) silver hexafluoroantimonate were suspended in chlorobenzene (40 ml). The resulting mixture was stirred at room temperature for 15 minutes. It was then filtered to removed precipitated AgCl. To the resulting gold-colored solution was added a solution of 6.46 g (21.2 mol) of the hexafluoroisopropanol-substituted norbornene and 1.00 g norbornene (10.62 mmol) dissolved in 5 mL chlorobenzene. The resulting reaction mixture was stirred overnight at room temperature. The reaction mixture was then concentrated to dryness and the polymer washed with hexane and dried in a vacuum oven. Yield=7.48 g of addition polymer. $^1H$ NMR ($CD_2Cl_2$) of the polymer was consistent with a random copolymer structure with the approximate molar composition shown below:

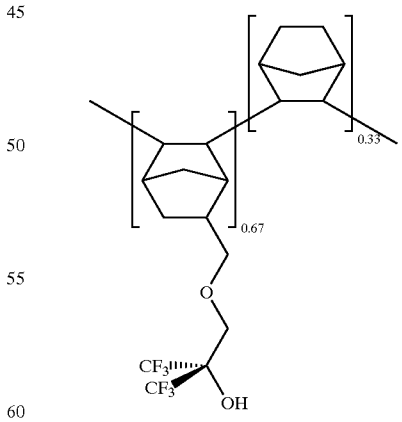

Example 14

Synthesis of 1,1-Bis(trifluoromethyl)-2-Chloromethyl Oxirane

Using 100 ml of NaOCl (Aldrich, 12% chlorine available), 0.5 g of phase transfer catalyst, tricaprylylmethylammonium chloride (Aliquat™-336, Aldrich) and 28 g of $(CF_3)_2C=CHCH_2Cl$, which is added slowly at 5–15° C., after stirring reaction mixture for 1 h at 15–20° C. and separation of layer, there is isolated 26 g of crude product, containing 84% epoxide and 16% of $(CF_3)_2CHCH=CHCl$ (NMR). Distillation of crude material using short spinning-band column give 7 g (78% calculated and 25% isolated yield respectively) of epoxide 98% purity, b.p. 88.2–88.6° C. NMR: $^1$H (acetone-d$_6$): 4.12 (1H, m), 3.95 (1H, m), 4.20 (1H, m); $^{19}$F: 74.11 (3F, q; 7 Hz), –67.21 (3F, q; 7 Hz); $^{13}$C (proton decoupled) 34.42 (q; 4 Hz), 58.94 (q; 3 Hz), 59.53 (sept.; 40 Hz), 120.37 (q.; 281 Hz), 120.96 (q.; 281 Hz). IR: 1459 cm$^{-1}$.

Example 15

Synthesis of 1,1-Bis(Perfluoroethyl)-2-n-Perfluoropropyl Oxirane

Using 18 ml of NaOCl (Aldrich, 12% chlorine available), 0.2 g of phase transfer catalyst (Aliquat™-336, Aldrich, tricaprylylmethylamonium chloride) and 3 g of $(C_2F_5)_2C=CHC_3F_7$, which is added slowly at 5–15° C., after stirring reaction mixture at 15–20° C. for 15 h, separation of lower layer it is isolated 2.5 g of crude product, which is based on NMR data epoxide of >98% purity. Yield is 83%. IR: 1354; 1353 cm$^{-1}$; $^1$H NMR.

(CDCl$_3$): 3.85 (d,d); $^{19}$F NMR: –81.55 (3F, d), –80.92 (3F, t), –81.10 (3F, t), –11.50 (2F, AB pattern), –119.00 (2F, AB pattern), –119.80 (2F, AB pattern), –127.80 (2F, AB pattern).

Example 16

Synthesis of $CH_2(O)C[C(CF_3)_2OH]C(O)OCH_3$ (3)

Using 30 ml of NaOCl (Aldrich, 12% chlorine available), 0.2 g of phase transfer catalyst (Aliquat-336, Aldrich, tricaprylylmethylamonium chloride) and 7 g of $CH_2=C[C(CF_3)_2 OH]C(O)OCH_3$, which is added slowly at 5–15° C., after stirring reaction mixture at 15–20° C. for 1.5 h, reaction mixture is filtered. There is isolated 4.0 g of product which, based on NMR data, is epoxide 3 of >98% purity, m.p. 56–58° C. Yield is 57%. IR: 1744; 1450 cm$^{-1}$; $^1$H NMR (CDCl$_3$): 3.15 (1H, d, 5.6 Hz) 3.25 (1H, d, 5.6 Hz); 3.87 (3H, s), 4.7 (1H, br.s); $^{19}$F NMR: –66.39 (3F, q, 7.2 Hz), –73.28 (3F, q, 7.2 Hz).

Example 17

Synthesis of $CH_2(O)C[C(CF_3)_2OH]C(O)OCH_3$ (4)

Using 18 ml of NaOCl (Aldrich, 12% chlorine available), 0.2 g of phase transfer catalyst (Aliquat-336, Aldrich, tricaprylylmethylamonium chloride) and 4 g of $CH_2=C[C(CF_3)_2 OH]C(O)OCH_3$, which is added slowly at 5–15° C., after stirring reaction mixture at 15–20° C. for 1.5 h, reaction mixture is filtered and there is isolated 2.5 g of product which, based on NMR data, is epoxide 4 of >98% purity, m.p. 148–150° C. Yield is 83%.

What is claimed is:

1. A method for producing a fluorinated epoxide comprising the step of reacting a fluorinated ethylenically unsaturated compound having the structure:

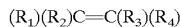

with a metal hypohalite oxidizing agent in the presence of a phase transfer catalyst to produce the fluorinated epoxide having the structure:

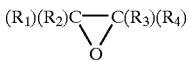

wherein $R_1$ is selected from the group consisting of H and OR, where R is $C_1$–$C_{10}$ alkyl; $R_2$ is selected from the group consisting of H, F, $C_1$–$C_{10}$ perfluoroalkyl, and X-substituted $C_1$–$C_{10}$ alkyl, wherein X is F, Cl, Br, I, OH, or OR; $R_3$ and $R_4$ are each independently selected from the group consisting of $C_1$–$C_{10}$ perfluoroalkyl, $C(R_f)(R_f')OH$, $C_1$–$C_{10}$ perfluoroalkoxy, $C_1$–$C_{10}$ carboalkoxy, and hydroxy-substituted $C_3$–$C_{10}$ carboalkoxymethyl-substituted $C_1$–$C_4$ perfluoroalkyl.

2. The method of claim 1 wherein $R_1$ is selected from the group consisting of H and OR, where R is $C_1$–$C_{10}$ alkyl; $R_2$ is selected from the group consisting of H and F; $R_3$ and $R_4$ are each independently selected from the group consisting of $C_1$–$C_{10}$ perfluoroalkyl and $C_1$–$C_{10}$ perfluoroalkoxy.

3. A method for producing a polyfluorinated polyether comprising the step of reacting a fluorinated epoxide having the structure:

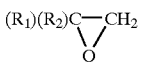

with a basic compound in solution to produce the polyfluorinated polyether having the repeat unit:

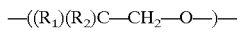

wherein $R_1$ and $R_2$ are independently $C_1$–$C_{10}$ perfluoroalkyl.

4. A fluorine-containing polymer comprising a repeat unit derived from at least one ethylenically unsaturated compound containing a fluoroalcohol functional group having the structure:

wherein $R_f$ and $R_f'$ are the same or different fluoroalkyl groups of from 1 to 10 carbon atoms or taken together are $(CF_2)_n$ wherein n is 2 to 10; and X is selected from the group consisting of sulfur, oxygen, nitrogen, phosphorous and any other element selected from Group Va and Group VIa.

5. The polymer of claim 4 wherein $R_f$ and $R_f'$ are $CF_3$ and X is oxygen.

6. A perfluorinated epoxide having the structure:

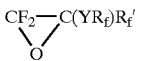

where $R_f$ and $R_f'$ are are the same or different perfluoroalkyl groups of from 1 to 10 carbon atoms or taken together are $(CF_2)_n$ wherein n is 2 to 10; and Y is selected from the group consisting of sulfur and oxygen.

7. The perfluorinated 2-alkoxypropene epoxide of claim 6 wherein Y is oxygen, $R_f$ is selected from the group consisting of trifluoromethyl, pentafluoroethyl and heptafluoropropyl, and $R_f'$ is trifluoromethyl.

8. A method for incorporating a fluoroalcohol functional group having the structure:

into a polymer as a pendant group, wherein $R_f$ and $R_f'$ are the same or different fluoroalkyl groups of from 1 to 10 carbon atoms or taken together are $(CF_2)_n$ wherein n is 2 to 10; and X is selected from the group consisting of sulfur, oxygen, nitrogen, phosphorous and any other element selected from Group Va and Group VIa;

said method comprising the steps of:

a. reacting an epoxide having the structure:

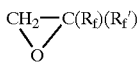

with an ethylenically unsaturated compound containing substituent X to produce an ethylenically unsaturated comonomer comprised of the structure:

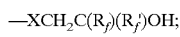

and b. polymerizing a reaction mixture comprised of the ethylenically unsaturated comonomer to produce the polymer.

9. The method of claim 8 where X is oxygen and $R_f$ and $R_f'$ are $CF_3$.

10. The polymer of claim 9 wherein the at least one ethylenically unsaturated compound is

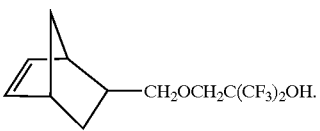

11. The method of claim 9 wherein the at least one ethylenically unsaturated compound is

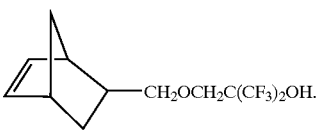

12. The method of claim 1 which $R_2$ is H.

* * * * *

UNITED STATES PATENT AND TRADEMARK OFFICE
CERTIFICATE OF CORRECTION

PATENT NO. : 6,653,419 B1  Page 1 of 1
APPLICATION NO. : 10/009037
DATED : November 25, 2003
INVENTOR(S) : Viacheslav Alexandrovich Petrov et al.

It is certified that error appears in the above-identified patent and that said Letters Patent is hereby corrected as shown below:

Col. 10,
Claim 8, line 63, $-XCH_2C(R_f)(R_{f)OH}$ should read -- $-XCH_2C(R_f)(R_f')OH$ --

Col. 11,
Claim 10, line 20, "The polymer of claim 9 wherein the at least one" should read --The polymer of claim 4 wherein the at least one--.

Signed and Sealed this

Fourteenth Day of November, 2006

JON W. DUDAS
*Director of the United States Patent and Trademark Office*